(12) United States Patent
Hasenoehrl (10) Patent No.: US 11,226,124 B2
(45) Date of Patent: Jan. 18, 2022

(54) SYSTEMS AND METHODS FOR COUPLING THE OPERATIONS OF AN AIR HANDLING DEVICE AND A VOLATILE COMPOSITION DISPENSER

(71) Applicant: The Procter & Gamble Company, Cincinnati, OH (US)

(72) Inventor: Erik John Hasenoehrl, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 848 days.

(21) Appl. No.: 14/879,110

(22) Filed: Oct. 9, 2015

(65) Prior Publication Data
US 2017/0102156 A1    Apr. 13, 2017

(51) Int. Cl.
*F24F 11/30* (2018.01)
*A61L 9/12* (2006.01)
(Continued)

(52) U.S. Cl.
CPC ............... *F24F 11/30* (2018.01); *A61L 9/032* (2013.01); *A61L 9/12* (2013.01); *A61L 9/122* (2013.01); *A61L 9/127* (2013.01); *A61L 9/14* (2013.01); *F24F 3/16* (2013.01); *F24F 11/62* (2018.01); *G05B 15/02* (2013.01); *A61L 2209/11* (2013.01); *A61L 2209/111* (2013.01); *A61L 2209/132* (2013.01); *A61L 2209/135* (2013.01);
(Continued)

(58) Field of Classification Search
CPC ........... G05B 15/02; A61L 9/12; F24F 11/006
USPC ......................................................... 700/276
See application file for complete search history.

(56) References Cited

U.S. PATENT DOCUMENTS 2,608,436 A * 12/1948 Baughman .............. A61L 9/127
299/20
3,917,165 A    11/1975 Cross
(Continued)

FOREIGN PATENT DOCUMENTS

CN    103830763 A    6/2014
EP    2541155 A1    1/2013
(Continued)

OTHER PUBLICATIONS

PCTUS2016/055869; 14 Pages; Dated Dec. 21, 2016.
(Continued)

*Primary Examiner* — Ryan D. Coyer
(74) *Attorney, Agent, or Firm* — Abbey A. Lopez (57) ABSTRACT

A system for circulating a volatile composition throughout at least one room is provided. The system includes a central communication unit capable of receiving incoming signals and sending outgoing instructions. The central communication unit comprises a memory configured to store settings. The system includes a volatile composition dispenser capable of delivering the volatile composition into the air. The volatile composition dispenser is communicably connectable with the central communication unit through a wireless communication link. The system includes an air handling device communicably connectable with the central communication unit and configured to move air throughout the at least one room upon receipt of an outgoing instruction from the central communication unit.

9 Claims, 6 Drawing Sheets

(51) Int. Cl.
*F24F 3/16* (2021.01)
*A61L 9/14* (2006.01)
*A61L 9/03* (2006.01)
*F24F 11/62* (2018.01)
*G05B 15/02* (2006.01)
*F24F 110/60* (2018.01)
*F24F 110/50* (2018.01)
*F24F 8/50* (2021.01)

(52) U.S. Cl.
CPC .......... *A61L 2209/16* (2013.01); *F24F 8/50* (2021.01); *F24F 2110/50* (2018.01); *F24F 2110/60* (2018.01)

(56) References Cited

U.S. PATENT DOCUMENTS

| | | |
|---|---|---|
| 5,924,597 A | 7/1999 | Lynn |
| 6,267,297 B1 | 7/2001 | Contadini et al. |
| 7,154,579 B2 | 12/2006 | Selander et al. |
| 7,469,844 B2 | 12/2008 | Conway et al. |
| 7,687,744 B2 | 3/2010 | Walter et al. |
| 7,786,889 B2 | 8/2010 | Van Der Poel et al. |
| 8,170,405 B2 | 5/2012 | Harris |
| 8,249,731 B2 | 8/2012 | Tran et al. |
| 8,620,841 B1 | 12/2013 | Filson et al. |
| 8,727,611 B2 | 5/2014 | Huppi et al. |
| 8,886,785 B2 | 11/2014 | Apte et al. |
| 8,892,261 B2 | 11/2014 | Hoonhout et al. |
| 8,930,030 B2 | 1/2015 | Bester et al. |
| 8,955,765 B2 | 2/2015 | Porchia et al. |
| 9,103,555 B2 | 8/2015 | Zou et al. |
| 9,113,052 B1 | 8/2015 | Scalisi et al. |
| 9,115,908 B2 | 8/2015 | Shetty et al. |
| 9,327,046 B2 | 5/2016 | Turner et al. |
| 9,352,063 B2 | 5/2016 | Ooten |
| 9,439,995 B2 | 9/2016 | Conroy |
| 9,452,234 B2 | 9/2016 | Conroy |
| 9,474,824 B2 | 10/2016 | Conroy |
| 9,691,214 B2 | 6/2017 | Chan |
| 9,738,125 B1 | 8/2017 | Brickley et al. |
| 9,804,398 B2 | 10/2017 | Watanabe |
| 9,804,578 B2 | 10/2017 | Deilmann |
| 9,808,550 B2 | 11/2017 | Fantuzzi |
| 9,857,810 B2 | 1/2018 | Smith, Jr. |
| 9,927,789 B2 | 3/2018 | Chandler et al. |
| 10,258,713 B2 | 4/2019 | Becker |
| 2003/0040813 A1 | 2/2003 | Gonzales et al. |
| 2003/0164557 A1 | 9/2003 | Chung et al. |
| 2004/0163073 A1 | 8/2004 | Krzyzanowski et al. |
| 2004/0227857 A1 | 11/2004 | Mizushima |
| 2004/0265164 A1 | 12/2004 | Woo et al. |
| 2005/0129568 A1 | 6/2005 | Kubby et al. |
| 2005/0147523 A1* | 7/2005 | Laudamiel-Pellet ............... A01M 1/2077 422/5 |
| 2006/0142968 A1 | 6/2006 | Han et al. |
| 2006/0161270 A1 | 7/2006 | Luskin et al. |
| 2007/0043478 A1 | 2/2007 | Ehlers |
| 2007/0166575 A1 | 7/2007 | McLeod |
| 2007/0228183 A1 | 10/2007 | Kennedy |
| 2008/0058740 A1 | 3/2008 | Sullivan et al. |
| 2008/0206092 A1 | 8/2008 | Crapser |
| 2009/0177328 A1 | 7/2009 | Finley |
| 2009/0265037 A1 | 10/2009 | Bassa |
| 2009/0271003 A1 | 10/2009 | Van Houtert et al. |
| 2010/0196195 A1 | 8/2010 | Moschel |
| 2010/0288847 A1 | 11/2010 | Gruenbacher |
| 2011/0077758 A1 | 3/2011 | Tran et al. |
| 2011/0132992 A1 | 6/2011 | Hoppe |
| 2011/0200488 A1 | 8/2011 | Cennini et al. |
| 2012/0251989 A1* | 10/2012 | Wetmore ............... G09B 19/00 434/236 |
| 2013/0081541 A1* | 4/2013 | Hasenoehrl ............ A61L 9/035 96/222 |
| 2013/0082817 A1 | 4/2013 | Gruenbacher et al. |
| 2013/0190556 A1* | 7/2013 | Wetmore ............... A61M 21/02 600/28 |
| 2013/0261809 A1 | 10/2013 | Morrow |
| 2014/0023060 A1 | 1/2014 | Apte et al. |
| 2014/0057232 A1* | 2/2014 | Wetmore ............... G09B 19/00 434/236 |
| 2014/0067130 A1* | 3/2014 | Pillai ............... H04L 12/2816 700/275 |
| 2014/0188287 A1 | 7/2014 | Sabata |
| 2014/0265920 A1 | 9/2014 | Pederson |
| 2015/0001904 A1 | 1/2015 | Edwards |
| 2015/0019030 A1* | 1/2015 | Chandler ............ G05D 7/0629 700/283 |
| 2015/0030498 A1 | 1/2015 | Ooten |
| 2015/0044961 A1 | 2/2015 | Sugiyama |
| 2015/0116110 A1 | 4/2015 | Schuman |
| 2015/0160636 A1 | 6/2015 | Mccarthy, III |
| 2015/0297778 A1 | 10/2015 | Conroy |
| 2016/0040903 A1 | 2/2016 | Emmons et al. |
| 2016/0151917 A1 | 6/2016 | Faridi |
| 2016/0195856 A1 | 7/2016 | Spero |
| 2016/0199977 A1 | 7/2016 | Breazeal |
| 2016/0321564 A1 | 11/2016 | Imahara |
| 2017/0102159 A1 | 4/2017 | Hasenoehrl |
| 2017/0102718 A1 | 4/2017 | Hasenoehrl |
| 2017/0336815 A1 | 11/2017 | Smith, Jr. |
| 2017/0351271 A1 | 12/2017 | Hasenoehrl |

FOREIGN PATENT DOCUMENTS

| | | |
|---|---|---|
| JP | H0399670 U | 10/1991 |
| JP | H04161733 A | 6/1992 |
| JP | 2003042518 A | 2/2003 |
| JP | 2005102156 A | 4/2005 |
| JP | 2008033618 A | 2/2008 |
| JP | 2010096433 A | 4/2010 |
| JP | 2010130471 A | 6/2010 |
| JP | 2011151603 A | 8/2011 |
| JP | 2011259153 A | 12/2011 |
| KR | 20130003810 A | 1/2013 |
| KR | 20140039874 A | 4/2014 |
| KR | 20140125245 A | 10/2014 |
| KR | 20150040133 A | 4/2015 |
| WO | WO 2006/126139 A1 | 11/2006 |
| WO | WO 2010/058382 A1 | 5/2010 |
| WO | 2011134690 A1 | 11/2011 |
| WO | WO 2014/036133 A1 | 3/2014 |
| WO | WO 2014/040118 A1 | 3/2014 |
| WO | WO 2014/135990 A2 | 9/2014 |

OTHER PUBLICATIONS

PCTUS2016/055480; 16 Pages; Dated Dec. 19, 2016.
PCTUS2016/055487; 13 Pages; Dated Dec. 13, 2016.
U.S. Appl. No. 14/879,108, filed Oct. 9, 2015, Hasenoehrl et al.
U.S. Appl. No. 14/879,112, filed Oct. 9, 2015, Hasenoehrl et al.
"Febreze Home & Connect (Webinar: Making IoT Accessible)", youtube, Mar. 17, 2016 (Mar. 17, 2016), p. 6 pp., XP054978005,Retrieved from the Internet:URL:https://www.youtube.com/watch?v=EWCw93kTtOQ [retrieved on Jan. 10, 2018].
PCT US2017/056240; 51 Pages; Dated Jan. 19, 2018.
R. Stapler Et Al: "Pura Scents: Smart Air 1,2,4-6, Freshener Meets Smart Nightlight by Team 10 Pura Scents—Kickstarter" , ,Nov. 17, 2015 (Nov. 17, 2015), XP055439290, Retrieved from the Internet: URL:https://www.kickstarter.com/projects/1253223575/pura-scents-the-worlds-smartestair-reshener/description[retrieved on Jan. 9, 2018].
R. Stapler Et Al: "Pura Scents: Smart Air Freshener Meets Smart Nightlight", Nov. 17, 2015 (Nov. 17, 2015), XP055439784, Retrieved from the Internet: URL:https://www.kickstarter.com/projects/1253223575/pura-scents-the-worlds-smartestair-freshener/faqs[retrieved on Jan. 10, 2018].
14052-US_Third Party Opposition for Application Serial No. 16784346.5 pp. 31.
Ademoye, Oluwakemi A, and Gheorghita Ghinea; Synchronisation of olfactory-enhanced multimedia: Perspectives from an empirical (56) References Cited

OTHER PUBLICATIONS study, IEEE International Conference on Multimedia and Expo; pp. 1425-1428; Year 2008.
All Office Actions, U.S. Appl. No. 14/879,108.
All Office Actions; U.S. Appl. No. 14/879,112.
All Office Actions; U.S. Appl. No. 15/684,375.
Bartelt et al., "A Versatile and Quantitative Volatile-Delivery System for Laboratory Bioassays", Journal of Chemical Ecology, vol. 24, No. 3, 1998, pp. 535-558.
Ben, and Jenny Tillotson. "Design as a means of exploring the emotional component of scent"; Year 2006 ;pp. 1-16.
Bodhale, Asmita, and J. S. Kulkarni. "Arduino Based Vending Machine." International Journal of Engineering Technology, Management and Applied Sciences, May 2017, vol. 5, Issue 5, pp. 795-800.
Gehring, Sven, et al. "Mobile product customization." CH1'10 Extended Abstracts on Human Factors in Computing systems. ACM, 2010. pp. 3463-3468.
Gosain, Devashish, and Mohit Sajwan. "Aroma tells a thousand pictures: digital scent technology a new chapter in IT industry." Int.J. Curr. Eng. Tech 4; Year2014; pp. 2804-2812.
Matsukura et al., "Smelling Screen: Development and Evaluation of an Olfactory Display System for Presenting a Virtual Odor Source", IEEE transactions on visualization and computer graphics, vol. 19, No. 4, Apr. 2013, pp. 606-615.
Murray, Niall, The impact of scent type on olfaction-enhanced multimedia quality of experience.IEEE Transactions onSystems, Man, and Cybernetics: Systems47.9; pp. 2503-2515; Year: 2016.
Nakaizumi et al., "SpotScents: A Novel Method of Natural Scent Delivery Using Multiple Scent Projectors", Virtual RealityConference, IEEE, 2006, pp. 213-218.
Scent By A Wireless Web; pp. 1-13; Year 2005.
Yuan, Zhenhui, Gheorghita Ghinea, and Gabriel-Miro Muntean. "Quality of experience study for multiple sensorial media delivery." 2014 International Wireless Communications and Mobile Computing Conference (IWCMC). IEEE, 2014.pp. 1142-1146.

* cited by examiner

SYSTEMS AND METHODS FOR COUPLING THE OPERATIONS OF AN AIR HANDLING DEVICE AND A VOLATILE COMPOSITION DISPENSER

FIELD

The present disclosure is directed to a system and method for coupling the operations of an air handling device and a volatile composition dispenser.

BACKGROUND

Air handling devices, such as heating, ventilation, and air conditioning (HVAC) devices, are often used in buildings, such as homes, businesses, and offices, to maintain the interior of the building at a desired temperature. Thermostats are often used to control an air handling device within a building. Thermostats may be programmable to control the air handling device different at different times of day and/or days of the week.

Volatile composition dispensers exist in various forms, including non-energized devices that passively diffuse volatile compositions and energized devices that utilize energy in various forms to dispense, or assist in dispensing, a volatile composition. One issue with volatile composition dispensers is that it is often difficult to fill a room with a desired level of volatile composition. Volatile composition dispensers have been modified in various ways in order to try and address this issue. However, it would be beneficial to provide a system or method that is able to improve the dispersion of a volatile composition dispensed from various types of volatile composition dispensers.

SUMMARY

Aspects of the present disclosure include a system for circulating a volatile composition throughout at least one room, the system comprising a central communication unit capable of receiving incoming signals and sending outgoing instructions, the central communication unit comprising a memory configured to store settings. The system comprises a volatile composition dispenser capable of delivering the volatile composition into the air, wherein the volatile composition dispenser is communicably connectable with the central communication unit through a wireless communication link. The system further comprises an air handling device communicably connectable with the central communication unit and configured to move air throughout the at least one room upon receipt of an outgoing instruction from the central communication unit.

Aspects of the present disclosure also include a method of circulating a volatile composition throughout at least one room using an air handling device, the volatile composition being delivered into the room from a volatile composition dispenser, wherein the air handling device and the volatile composition dispenser are each communicably connectable with a central control unit, the method comprising the steps of: (a) sending a first outgoing instruction from the central control unit to the volatile composition dispenser to turn on the volatile composition dispenser; (b) sending a second outgoing instruction from the central control unit to the volatile composition dispenser to turn off the volatile composition dispenser after a first set point is reached; (c) sending a third outgoing instruction from the central control unit to the air handling device to turn on the air handling device at a second set point, wherein the second set point is a predetermined time relative to when the first set point is reached; (d) sending a fourth outgoing instruction from the central control unit to the air handling device to turn off the air handling device after a third set point is reached; and (e) optionally repeating steps (a) through (d).

DETAILED DESCRIPTION

While the methods and systems of the present disclosure will be described more fully it is to be understood at the outset of the description which follows that persons of skill in the appropriate arts may modify the methods and systems herein described while still achieving the favorable results of described in the present disclosure. Accordingly, the description which follows is to be understood as being a broad, teaching disclosure directed to persons of skill in the appropriate arts, and not as limiting upon the present disclosure.

The present disclosure includes systems and methods for coupling the operations of a volatile composition dispenser with the operation of an air handling device to improve the dispersion of a volatile composition throughout at least one room. By coupling the operation of the volatile composition dispenser and the operation of the air handling device, the dispersion of a volatile composition dispensed from the volatile composition dispenser can be optimized by the air flow from the air handling device.

The systems and methods include one or more air handling devices, a central communication unit (CCU) that is communicably connectable with the air handling system, and one or more volatile composition dispensers that are each communicably connectable with the CCU. The air handling device may include a fan for circulating air throughout at least one room of a building.

Figure 1:
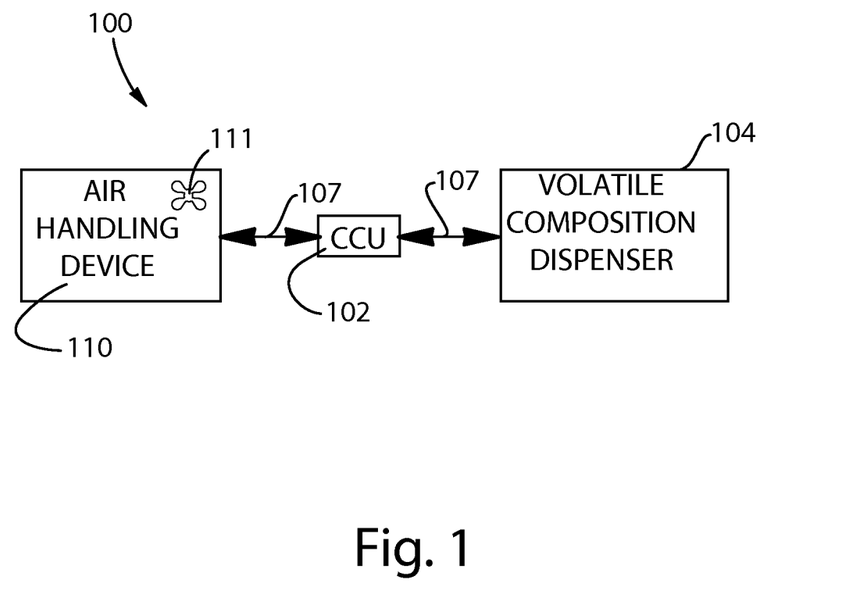
FIG. 1 illustrates exemplary components of a system having, a central communication unit, a volatile composition dispenser that communicates with the CCU through a wireless communication link, and an air handling device having a fan that is controlled by the CCU.

FIG. 1 illustrates exemplary components of the system 100, including the central communication unit 102, a volatile composition dispenser 104 that communicates with the CCU 102 through a wireless communication link 107, and an air handling device 110 having a fan 111 that is controlled by the CCU 102.

For example, the CCU 102 may run an algorithm that turns ON the volatile composition dispenser 104 for a first period of time in order to deliver a desired amount of volatile composition into the room. Then, either before or after the volatile composition dispenser 104 is turned off, or while the volatile dispenser is active, the CCU 102 may turn on the air handling device 110 in order to move air throughout the room.

The CCU 102 may be configured to turn on only the fan 111 of the air handling device 110 in order to circulate the volatile composition throughout the room. The CCU 102 may be configured to turn on the air conditioning or heat to control the climate within the at least one room.

As discussed in more detail below, the CCU comprises a memory that is capable of storing set points and algorithms and a processor that is capable of running algorithms and accessing the stored set points from the memory. The CCU is capable of running algorithms that couple the ON/OFF controls of the volatile composition dispenser with the ON/OFF controls on the air handling device. Various algorithms may be programmed depending upon the desired sequence of operations and the desired timing of each sequence.

In addition to the algorithm to couple the operation of the air handling device with the volatile composition dispenser, the CCU may also include an algorithm to control the temperature within the at least one room of the building. The algorithm to control the temperature may be a primary operation that takes precedence over a secondary algorithm to couple the volatile composition dispenser operation with the air handling device in order to ensure that the at least one room is maintained at a comfortable temperature.

Figure 2:
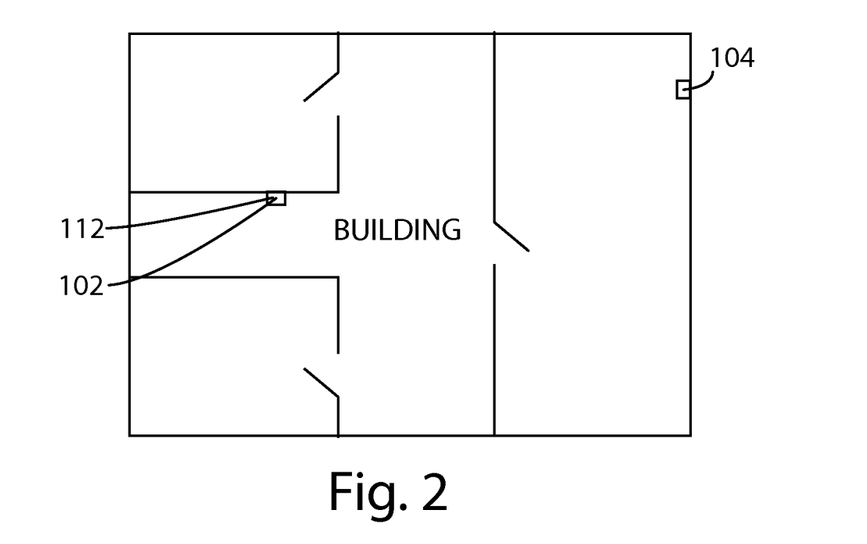
FIG. 2 illustrates a volatile composition dispenser that is placed in a different room from the placement of a CCU.

The volatile composition dispenser 104 may be placed in any room of a building. As shown in FIG. 2, the volatile composition dispenser 104 may be placed in a different room from the placement of the CCU 102. The CCU in FIG. 2 is shown as a thermostat 112 for exemplary purposes only. Additionally, the volatile composition dispenser 104 may be moved to different rooms at the user's convenience.

Air Handling System

The system 100 may include an air handling device 110. Air handling device 110 includes a fan 111. The air handling device 110 may provide heating, ventilation, air condition (HVAC) and/or air handling to an enclosure, such as a single-family home, apartment, office building, business, and the like. The air handling device 110 may be configured as a forced air type heating and cooling system. However, the air handling device 110 may be configured in various different ways. For example, the air handling device 110 may be configured in the form of a heat-pump based system; fan, including ceiling fan or portable fan; portable air conditioner; and/or portable heater.

The air handling device 110 may have one or more controls. The controls on the air handling device 110 may include turn ON/OFF the heater, turn ON/OFF the air conditioner, and/or turn ON/OFF the fan only. It is to be appreciated that the fan may also run when the heater or air conditioner is ON in order to push the heated or cooled air throughout the at least one room of the building.

The air handling device 110 may include a wireless communication module 117 in order to be wirelessly connected with various components of the system 100, such as the CCU 102, the volatile composition dispenser 104, and/or the smart appliance, through a wireless communication link.

Figure 3:
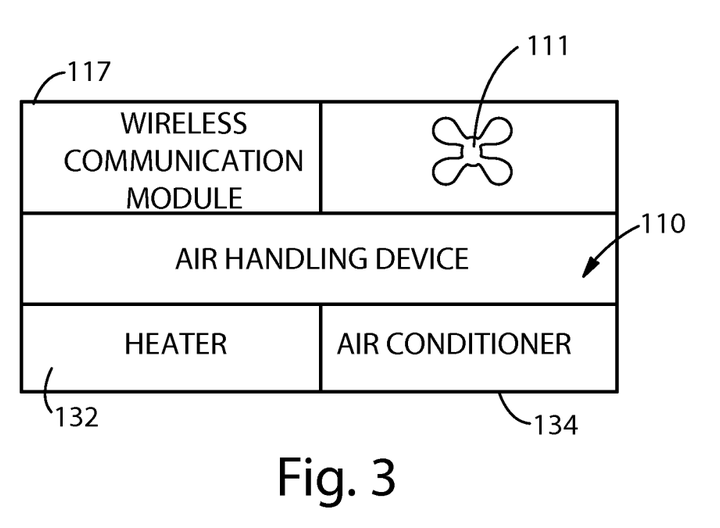
FIG. 3 illustrates an exemplary air handling device having a fan.

FIG. 3 illustrates an exemplary air handling device 110. As shown in FIG. 3, the air handling device 110 may include a fan 111, a heater 132, an air conditioner 134, and/or a wireless communication module 117. However, it is to be appreciated that the air handling device 110 may include only some of the components shown in FIG. 3.

Volatile Composition Dispenser

A volatile composition dispenser 104 may be used for the delivery of a volatile composition to the atmosphere or onto an inanimate surface. Such volatile composition dispenser 104 may be configured in a variety of ways. The volatile composition dispenser may include a wireless communication module 114 in order to establish a wireless communication link 107 with various components of the system 100. The volatile composition dispenser may additionally include mesh network border router functionality.

For example, the volatile composition dispenser 104 may be configured for use as an energized dispenser (i.e. powered by electricity; or chemical reactions, such as catalyst fuel systems; or solar powered; or the like). Exemplary energized volatile composition dispensers include a powered delivery assistance means which may include a heating element, a piezo element, thermal ink jet element, fan assembly, or the like. More particularly, the volatile composition dispenser may be an electrical wall-plug volatile composition dispenser, a non-limiting example of an electrical wall-plug volatile composition dispenser is described in U.S. Pat. No. 7,223,361; a battery (including rechargeable battery) powered volatile composition dispenser having a heating and/or fan element. In energized devices, the volatile material delivery engine may be placed next to the powered delivery assistance means to diffuse the volatile material. The volatile material may be formulated to optimally diffuse with the delivery assistance means.

The volatile composition dispenser 104 may be configured for use as a non-energized dispenser. An exemplary non-energized volatile composition dispenser includes a reservoir and, optionally, capillary, wicking means, or an emanating surface, to help volatile materials passively diffuse into the air (i.e. without an energized means). A more specific example a volatile composition dispenser includes a delivery engine having a liquid reservoir for containing a volatile material and a microporous membrane enclosing the liquid reservoir as disclosed in U.S. Pat. Nos. 8,709,337 and 8,931,711.

The volatile composition dispenser 104 may also be configured for use as an aerosol sprayer or a non-aerosol air sprayer. The volatile composition dispenser 104 can be programmed to automatically deliver a volatile composition to the atmosphere.

The volatile composition dispenser 104 may be configured in the form of an air purifying system to deliver both purified air and/or volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

The volatile composition dispenser 104 may be movable to different rooms within a housing or building. Moreover, a house or building may include one or more volatile composition dispensers that are positioned in the same room or in different rooms.

Volatile Composition

The volatile composition may be an air freshening composition, including a perfume composition and/or a malodor control composition. The volatile composition may be an insect repellant.

The volatile composition may comprise volatile materials. Exemplary volatile materials include perfume materials, volatile dyes, materials that function as insecticides, essential oils or materials that acts to condition, modify, or otherwise modify the environment (e.g. to assist with sleep, wake, respiratory health, and like conditions), deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

The volatile composition may include perfume ingredients to provide a desirable scent in the air. The volatile composition includes a mixture of volatile aldehydes that are designed to deliver genuine malodor neutralization (and not function merely by covering up or masking odors). A genuine malodor neutralization provides a sensory and analytically measurable (e.g. gas chromatograph) malodor reduction. Thus, if the volatile composition delivers genuine malodor neutralization, the volatile composition will reduce malodors in the vapor and/or liquid phase. The volatile composition may comprise a mixture of volatile aldehydes that neutralize malodors in vapor and/or liquid phase via chemical reactions. Such volatile aldehydes are also called reactive aldehydes. Volatile aldehydes may react with amine-based odors, following the path of Schiff-base formation. Volatiles aldehydes may also react with sulfur-based odors, forming thiol acetals, hemi thiolacetals, and thiol esters in vapor and/or liquid phase.

The volatile composition may include various other ingredients, including, but not limited to: surfactants; acid catalysts; polymers; buffering agents; solubilizers; antimicrobial compounds; preservatives; wetting agents; aqueous carrier; diluents; the like; and combinations thereof.

Sensors

One or more components of the system 100 may include a sensor 106. For example, the volatile composition dispenser 104, the CCU 102, the air handling device, or a smart appliance may include one or more sensors 106. The sensors 106 may be configured to sense temperature, relative humidity, air quality, $CO_2$ levels, air particle counters, and allergens and other air borne entities that have effect on human health. The sensor 106 may include a wireless communication module in order to be communicably connectable with the CCU and various components of the system through a wireless communication link.

The sensor 106 may be powered by a power source 118. The sensor 106 may be powered independently from the volatile composition dispenser 104 or through the same power source of the volatile composition dispenser 104. The sensor 106 may be powered by a battery independently from the volatile composition dispenser 104 or by a battery configured to also power the volatile composition dispenser 104. The volatile composition dispenser and/or the sensor 106 may be powered through an electrical outlet. Battery power is used when the volatile composition dispenser is a mobile device that can be moved around from room to room or surface to surface. Moreover, a battery may be used to power the sensor 106 when the volatile composition dispenser is configured as a non-energized device that passively diffuses volatile compositions into the air.

The sensor is configured to send sensor measurements to the CCU in the form of incoming signals. The sensor measurements can be used in a variety of ways. For example, the sensor measurements may be viewed as live data; compared with set points, such as temperature set points in order to control the air handling device; or stored in a database for further analysis to recommend optimum set points taking comfort and energy efficiency into consideration.

Figure 4:
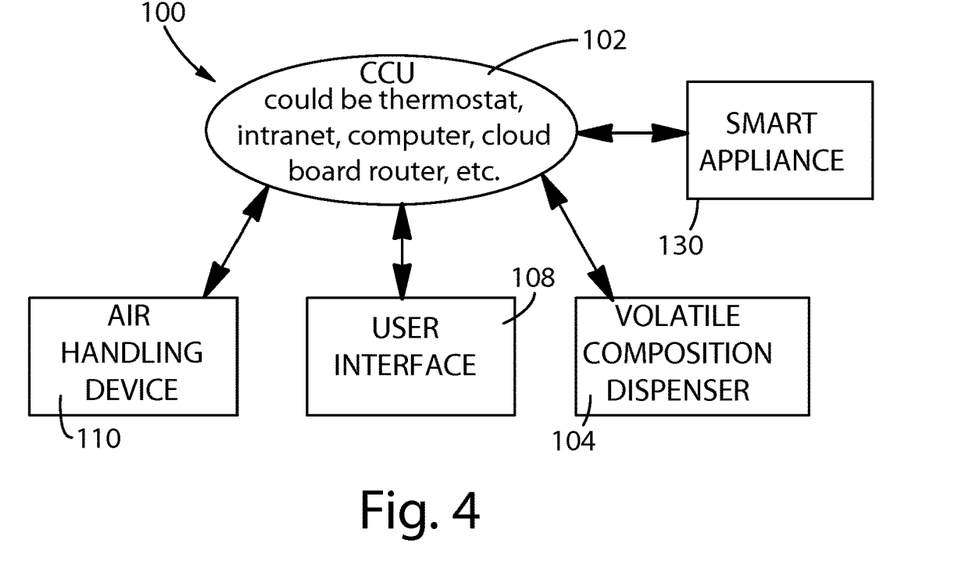
FIG. 4 depicts multiple possible flows of sensor measurements to either view the sensor measurements live or store for analysis.

FIG. 4 depicts multiple possible flows of signals from the components of the system. Sensor measurements can flow through the CCU to a user interface for live local sensor measurements. Alternatively, the sensor measurements can also pass from the sensor through the CCU to a destination server on the internet where it is stored in memory or analyzed by a processor in order to send instructions to the various components, including, but not limited to, the air handling device 110 and volatile composition dispenser 104.

Central Communications Unit

The CCU 102 can be configured in various different ways. The CCU 102 may be configured to receive incoming signals from the one or more components of the system 100 and send outgoing instructions to one or more components of the system 100, for example the air handling device and/or the volatile composition dispenser.

Figure 5:
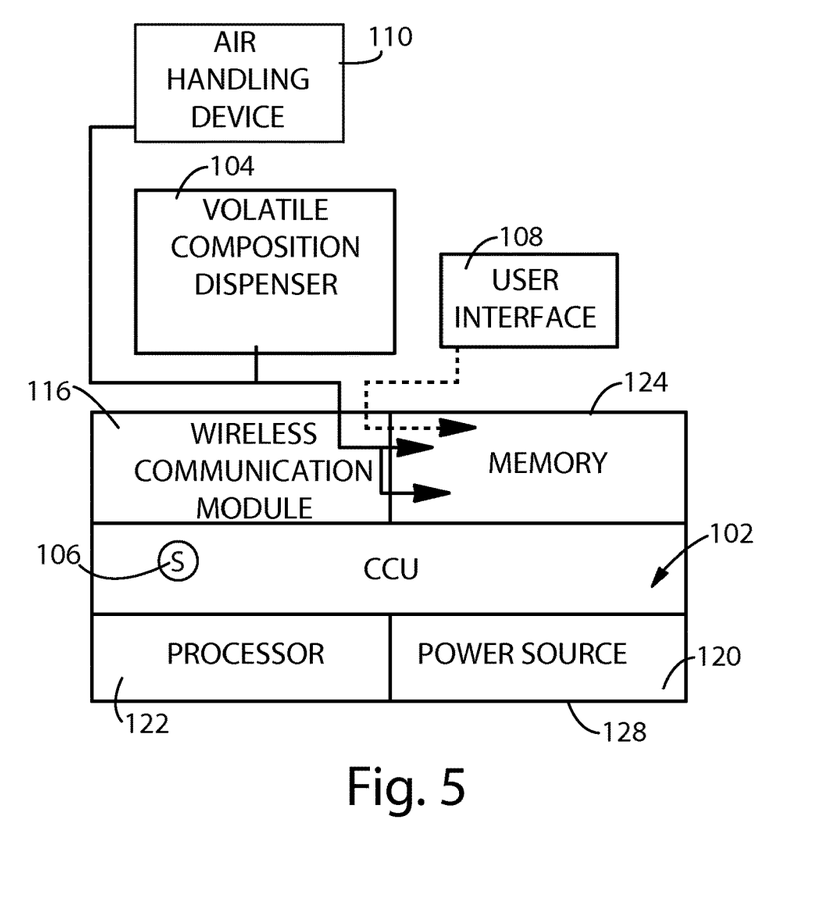
FIG. 5 illustrates an exemplary CCU having the processor and the memory disposed within a housing.

With reference to FIG. 5, the CCU 102 may be communicably connectable with various components of the system 100, including the sensor(s) 106, user interface(s) 108, and/or smart appliances using a wireless communication link 107. Various wireless communication links may be used, including 802.11 (Wi-Fi), 802.15.4 (ZigBee, 6LoWPAN, Thread, JennetIP), Bluetooth, combinations thereof, and the like. Connection may be through an ad hoc Mesh Network protocol. The CCU 102 may include a wireless communication module 116 in order to establish a wireless communication link 107 with the CCU 102 with various components of the system. Any module known in the art for establishing such communication links can be utilized.

The CCU 102 may comprise a processor 122. The processor 122 may be configured and programmed to carry out and/or cause to be carried out the one or more advantageous functionalities of the system 100 described herein. The processor 122 may be physically disposed within a CCU 102 or may be remotely located on a computer, special computer, smart device such as a phone or tablet, server, intranet, border router, cloud-based system, the like, or combinations thereof. The processor 122 can carry out algorithms stored in local memory; special-purpose processors or application-specific integrated circuits; algorithms carried out or governed remotely by central servers, or cloud-based systems, such as by virtue of running a Java virtual machine that executes instructions provided from a cloud server using Asynchronous Javascript and XML or similar protocols.

The CCU 102 may comprise a memory 124. The memory may be configured to store set points; incoming signals, such as sensor measurements and status indicators; algorithms; and the like. The memory may be a local memory within the CCU 102 such as a flash drive, hard drive, read only memory, or random access memory. Or, the memory may be configured as remote memory on a computer, smart device such as a phone or tablet, on a server, or on cloud-based system. The memory 124 can be accessible to the processor 122 in a variety of ways.

The processor and/or the memory of the CCU 102 may be disposed within a housing of the CCU 102. The CCU 102 may be connected with or separate from various components of the system 100. For example, the CCU 102 may be physically connected with the air handling device 110 or the volatile composition dispenser 104. The CCU 102 may be permanently positioned in a building in a separate room or location from other components such as the air handling device 110, the volatile composition dispenser 104, and/or a smart appliance, for example.

The CCU may include a clock or may be communicably connectable with a clock on a computer, smart device, or on the internet.

The CCU 102 may also include a sensor 106. The CCU may be configured to receive incoming signals of sensor measurements from both the volatile composition dispenser 104 and/or directly from the CCU 102.

FIG. 5 illustrates an exemplary CCU 102 having the processor 122 and the memory 124 disposed within a housing 128. The CCU 102 shown in FIG. 5 may be disposed on or within a volatile composition dispenser 104, an air handling device 110, and/or a smart appliance. While FIG. 5 illustrates a processor 122 and a memory 124 disposed within the housing 128, it is to be appreciated that the processor 122 and/or the memory 124 may be remotely located relative to the CCU 102.

The CCU 102 may be communicably connected with the air handling device 110 in various ways. For example, the CCU 102 may be electrically wired to the air handling device 110. The CCU 102 may be communicably connectable with the air handling device through a wireless connection link.

Incoming signals may pass through a CCU unit comprising a transmitter that transmits the incoming signals to the remote memory. Incoming signals may also be directly received by a component that is wirelessly communicating with the component sending the signals.

Figure 6:
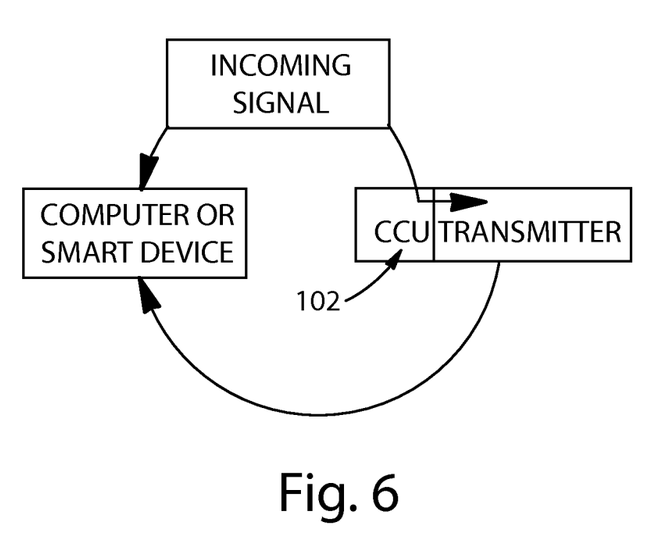
FIG. 6 illustrates multiple exemplary flows of incoming signals to a remote memory.

FIG. 6 illustrates multiple exemplary flows of incoming signals to a remote memory. The incoming signals may flow directly to a computer or smart device through a wireless communication link or through a transmitter of the CCU to a remote memory. The processor 122 may access the incoming signals from the memory 124. The processor 122 may access the memory 124 through a wired or wireless communication link.

The processor 122 may be configured to compare incoming signals to set points stored in the memory 124. The processor is able to retrieve stored set points from the memory 124 to compare.

Figure 7:
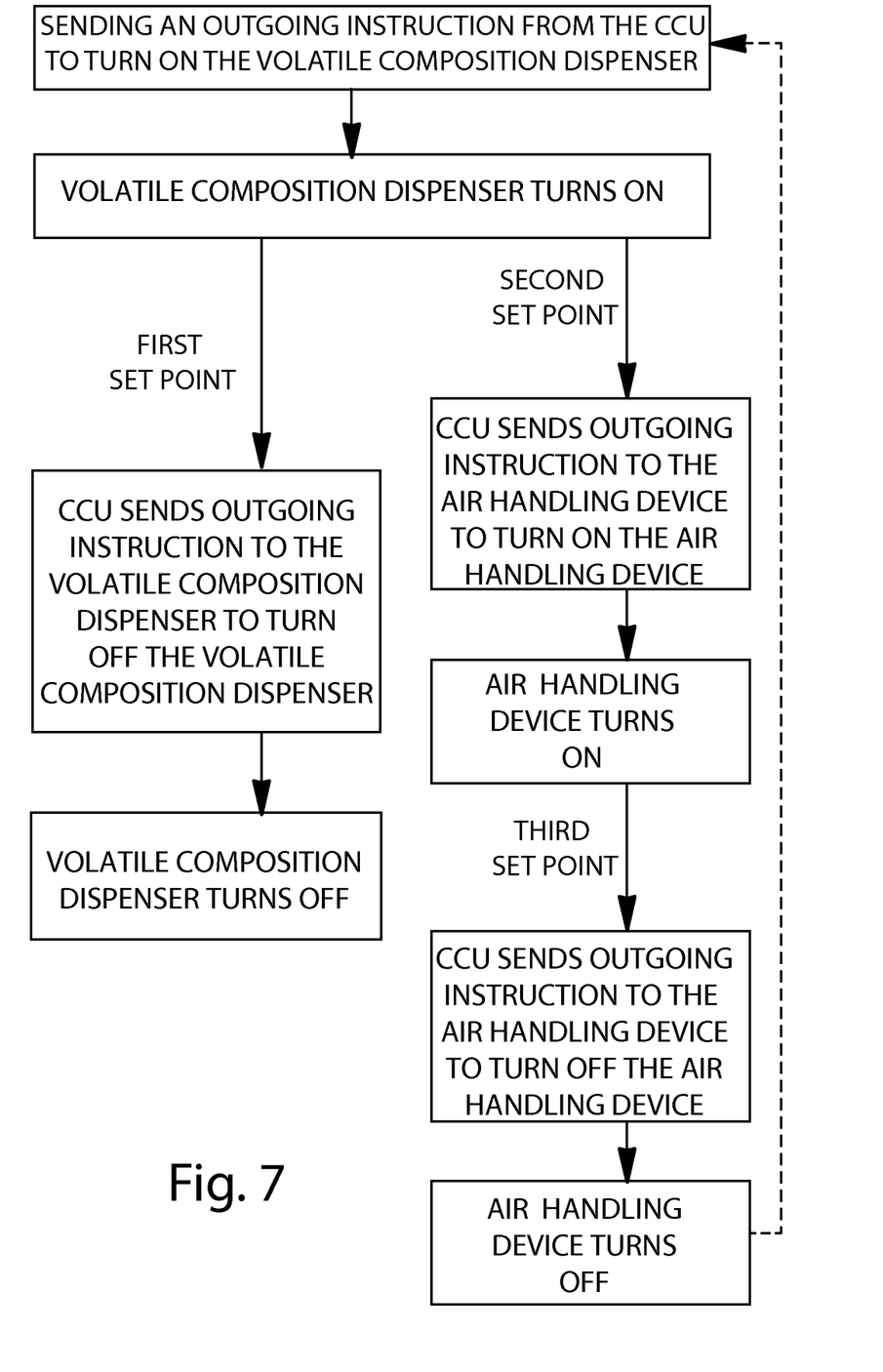
FIG. 7 illustrates an exemplary algorithm that couples the operation of a volatile composition dispenser with the operation of an air handling device.

As discussed above, the CCU may be figured to run various algorithms that couple the operation of the volatile composition dispenser with the operation of the air handling device. FIG. 7 illustrates an exemplary algorithm that couples the operation of the volatile composition dispenser 104 with the operation of the air handling device 110. The algorithm may include the steps of sending an outgoing instruction from the CCU 102 to the volatile composition dispenser 104 that tells the volatile composition dispenser 104 to turn ON for a period of time. The period of time that the volatile composition dispenser 104 is set to be ON may be programmed as a first set point in the algorithm. It is to be appreciated that the set points may be described as a first, second, third, etc. in the following description and the same set point may have a different name in the claims or in a different algorithm description depending upon which set point is described first. Once the first set point has been reached, the CCU may send an outgoing instruction to the volatile composition dispenser 104 to turn OFF. The CCU may send an outgoing instruction to the air handling device 110 to turn ON the air handling device 110 at a predetermined time relative to when the first set point is reached, which may be programmed in the algorithm as a second set point. The algorithm may include a third set point for the amount of time that the air handling device 110 is to remain ON. Once the third set point is reached, the CCU sends an outgoing instruction to the air handling device 110 to turn OFF. The algorithm can repeat indefinitely or for a preprogrammed number of iterations.

The algorithm may be adjusted to change the first, second, third, and any additional set points. For example, user may utilize a user interface in order to adjust the set points, including the first, second, and third set points described above for exemplary purposes.

The set points may be a duration of time; a temperature, a level of volatile composition dispensed, a current condition of a component, or the like. The processor may utilize various components in order to determine when a set point has been reached. For example, a clock, which may be connected with the CCU or remotely located on a computer, smart device, or on the internet, may be used to measure a duration of time. In another example, a sensor may be used to measure various conditions, such as the current temperature of level of volatile composition in the air. The sensor may be located on any component of the system or remote from the components of the system. The set point may also be based on a condition of a component. For example, a set point may be that a component is turned ON or OFF, which may signal the CCU to move on to the next step in the algorithm. The status of a component may be communicated to the CCU.

For example, the first and third set points described above with regard to FIG. 7 are durations of time. The first set point is a time duration in the range of about 5 minutes to about 60 minutes. the third set point is a time duration in the range of about 5 minutes to about 20 minutes. The second set point is before the first set point, at the same time as the first set point, or after the first set point.

An algorithm may include sending an outgoing instruction from the CCU to the air handling device 110 to turn ON the air handling device 110 while the volatile composition dispenser 104 has been ON for a period of time that is less than the total time the volatile composition dispenser 104 is programmed to stay ON. As such, there may be an overlapping period of time where the volatile composition dispenser 104 and the air handling device 110 are both ON.

A non-limiting example may include using a volatile composition dispenser, such as a FEBREZE® NOTICEABLES® plug-in air freshener for exemplary purposes only, comprising one or more of a 802.15.4 or 802.15.11 wireless radio and configured to emit a volatile composition for a duration of time of about 45 minutes. After 45 minutes, the FEBREZE® NOTICEABLES® plug-in air freshener stops emitting the volatile composition and wirelessly sends a command to a CCU, such as a NEST® learning thermostat, to activate an air handling device, such as an HVAC fan, for a duration of time of about five minutes to about 15 minutes. After the HVAC fan runs for between about five minutes and 15 minutes, the FEBREZE® NOTICEABLES® plug-in air freshener sends another signal to the NEST® learning thermostat to turn the fan of the HVAC off. The cycle may be repeated.

The memory 124 may be configured to store multiple set points. For example, there may be different set points for different times, time periods of a day and there may be different set points for different days of the week. The processor may include a clock in determine which set point is to be used for a particular time of day and/or day of the week.

The processor may be configured to use outgoing signals or sensor measurements from different components located within a house or building at different times of the day and/or different days of the week. For example, a first volatile composition dispenser may be located in a first room of a house and a second volatile composition dispenser may be located in a second room of the house that is separate from the first room. The CCU may be programmed to utilize the incoming signals of the first volatile composition dispenser at a first time period and/or on a first day and the CCU may be programmed to utilize the incoming signals of the second volatile composition dispenser at a second time period and/or on a second day that is different from the first time period and/or first day. As a result, the system can control the disperion of a volatile composition within one room at one time of day or day of the week and control the disperion of a volatile composition within a second room at another time or day or day of the week. Moreover, an algorithm may be set to alternate coupling the operation of the air handling device with the operation of the two or more volatile composition dispensers to help disperse volatile compositions within multiple rooms throughout the day.

The CCU may be configured as a thermostat such as the thermostat shown in FIG. 2. Power for the thermostat may be scavenged from the control wires that connect the air handling device to the thermostat. The thermostat may include a processor or memory, or the thermostat may communicate with a remote processor and/or memory. The thermostat may include a user interface. The thermostat may be a NEST® learning thermostat, a LUTRON® thermostat etc.

The processor may compute optimal set points from an algorithm based on user preferences of volatile composition levels and air handling device operation profiles based on historical sensor measurements, historical set points, and known information on energy efficiency, comfort, and volatile composition levels. The algorithm may be a machine learning algorithm. A machine learning algorithm can learn a user(s) preferred set points at various times of day and/or days of the week and/or can be used to program a more energy efficient algorithm, for example. An exemplary learning system is used in a NEST® learning thermostat. An exemplary learning system is also described in U.S. Pat. No. 9,115,908. The processor then transmits the optimal set points to the memory which then stores the set points for control of the HVAC.

Devices, including the air handling device, volatile composition dispenser, and/or smart appliance(s), of the system may interact with each other through the CCU such that events detected by one device may influence actions of another device or the current status of one device may influence actions of another device.

User Interface

The systems and methods of the present disclosure may include one or more user interfaces 108. The user interface 108 may be configured in various different forms. A user can interact with the user interface 108 to adjust set points as well as connect the sensors 106 through the CCU 102 for viewing of live sensor data on the user interface. The CCU 102 could also connect to the internet or intranet and pass through information, such as sensor measurements and the set points to a server for the purpose of remote monitoring on a user interface 108.

Figure 8:
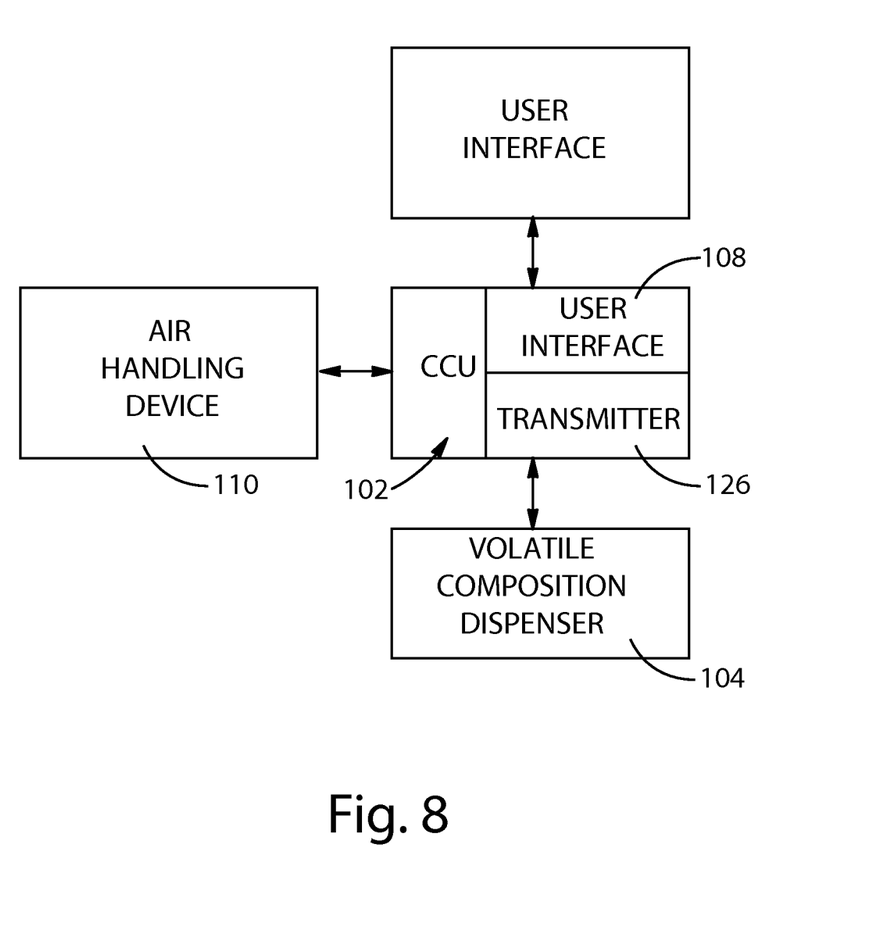
FIG. 8 illustrates an exemplary system having more than one user interface.

FIG. 8 illustrates an exemplary system having more than one user interface. In FIG. 8, a first user interface is connected with the CCU and a second user interface is a remote user interface. The remote user interface may be in the form of a computer or handheld smart device.

Where the CCU is configured as a thermostat, the thermostat may include a user interface where the user can adjust temperature set points by pushing buttons or turning dials, for example.

The user interface may be configured as a program, HTML website, or a Native application that is accessible by a user through a computer or handheld smart device. A handheld smart device may include an iPhone®, iPad®, or an Android® or Microsoft® based system. The user interface may be accessible on a computer such as a desktop, laptop, or tablet.

The system of the present disclosure may include a handheld smart device or computer that comprises the CCU 102, including the processor 122, memory 124, and/or user interface 108.

Smart Appliances

Various different smart appliances may also be connected with the system and included in the methods of the present disclosure. The smart appliances may be communicably connectable with the CCU. Smart appliances may include refrigerators, washers, dryers, dishwashers, microwaves, stoves, stereos, televisions, cable or satellite boxes, baby monitors, vacuum cleaners, security systems, lights, garage door openers, doorbell, indoor or outdoor sprinklers or irrigation systems, and the like.

The smart appliances may be configured to send an alert in the form of an incoming signal to the CCU, alerting the CCU that a particular smart appliance has been turned on or off. The smart appliance may also include sensors that are configured to send incoming signals to the CCU that alert the CCU as to current status of the smart appliance.

The CCU may also be configured initiate an algorithm that may include controlling a smart appliance based on sensor measurements sent to the CCU. The CCU may also be configured to control the volatile composition dispenser based upon the current status of a smart appliance.

Exemplary systems and methods that include coupling the operation of a smart appliance with the operation of a volatile composition dispenser are described in U.S. Patent Application, entitled "SYSTEMS AND METHODS FOR COUPLING THE OPERATIONS OF A VOLATILE COMPOSITION DISPENSER AND A SMART APPLIANCE", U.S. application Ser. No. 14/879,112, filed on Oct. 9, 2015. Exemplary systems and methods for controlling an air handling device with a volatile composition dispenser are described in U.S. Patent Application, entitled "VOLATILE COMPOSITION DISPENSER HAVING A TEMPERATURE SENSOR TO REMOTELY CONTROL AN AIR HANDLING DEVICE", U.S. application Ser. No. 14/879,108, filed on Oct. 9, 2015.

Values disclosed herein as ends of ranges are not to be understood as being strictly limited to the exact numerical values recited. Instead, unless otherwise specified, each numerical range is intended to mean both the recited values, any integers within the specified range, and any ranges with the specified range. For example a range disclosed as "1 to 10" is intended to mean "1, 2, 3, 4, 5, 6, 7, 8, 9, 10." It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Values disclosed herein as ends of ranges are not to be understood as being strictly limited to the exact numerical values recited. Instead, unless otherwise specified, each numerical range is intended to mean both the recited values, any integers within the specified range, and any ranges with the specified range. For example a range disclosed as "1 to 10" is intended to mean "1, 2, 3, 4, 5, 6, 7, 8, 9, 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for circulating a volatile composition throughout at least one room, the system comprising:
    a central communication unit capable of receiving incoming signals and sending outgoing instructions, the central communication unit comprising a memory configured to store settings;
    a volatile composition dispenser capable of delivering the volatile composition into the air of the at least one room, wherein the volatile composition dispenser is communicably connectable with the central communication unit through a wireless communication link, wherein the volatile composition dispenser is movable throughout the at least one room or movable into a different room; and
    an air handling device communicably connectable with the central communication unit and configured to move air throughout the at least one room upon receipt of an outgoing instruction from the central communication unit wherein the central communication unit sends an outgoing instruction to the air handling device to turn on after the volatile composition dispenser sends a signal to the central communication unit that the volatile composition dispenser is turned off.

2. The system of claim 1, wherein the wireless communication link is selected from the group consisting of: Wi-Fi; Bluetooth; ZigBee, 6LoWPAN, Thread, Mesh Network, or combinations thereof.

3. The system of claim 1, wherein the volatile composition dispenser comprises a sensor for measuring temperature or level of volatiles in the air.

4. The system of claim 1, wherein the volatile composition dispenser is configured with mesh network border router functionality.

5. The system of claim 1, wherein the volatile composition dispenser is a heating, ventilation, and air conditioning system.

6. The system of claim 1, wherein the volatile composition dispenser is communicably connectable with an ad hoc wireless mesh network.

7. The system of claim 1, wherein at least two volatile composition dispensers are communicably connectable with the central communication unit.

8. The system of claim 1, wherein the central communication unit uses an algorithm to determine the optimal volatile composition levels and air handling device operation profiles.

9. The system of claim 8, wherein the algorithm is a machine learning algorithm.

* * * * *